United States Patent
Chowdhary et al.

(10) Patent No.: US 11,096,593 B2
(45) Date of Patent: Aug. 24, 2021

(54) METHOD FOR GENERATING A PERSONALIZED CLASSIFIER FOR HUMAN MOTION ACTIVITIES OF A MOBILE OR WEARABLE DEVICE USER WITH UNSUPERVISED LEARNING

(71) Applicants: STMicroelectronics, Inc., Coppell, TX (US); STMicroelectronics International N.V., Schiphol (NL)

(72) Inventors: Mahesh Chowdhary, San Jose, CA (US); Arun Kumar, New Delhi (IN); Ghanapriya Singh, New Delhi (IN); Rajendar Bahl, Gurugram (IN)

(73) Assignees: STMicroelectronics, Inc., Coppell, TX (US); STMicroelectronics International N.V., Schiphol (NL)

(*) Notice: Subject to any disclaimer, the term of this patent is extended or adjusted under 35 U.S.C. 154(b) by 6 days.

(21) Appl. No.: 16/783,569

(22) Filed: Feb. 6, 2020

(65) Prior Publication Data
US 2020/0229710 A1 Jul. 23, 2020

Related U.S. Application Data

(63) Continuation of application No. 15/600,057, filed on May 19, 2017, now Pat. No. 10,588,517.

(51) Int. Cl.
*A61B 5/0205* (2006.01)
*A63B 69/00* (2006.01)
(Continued)

(52) U.S. Cl.
CPC ........ *A61B 5/0205* (2013.01); *A61B 5/02438* (2013.01); *A61B 5/1123* (2013.01);
(Continued)

(58) Field of Classification Search
CPC . A61B 5/0205; A61B 5/02438; A61B 5/0245; A61B 5/1123; A61B 5/222;
(Continued)

(56) References Cited

U.S. PATENT DOCUMENTS

| 8,930,300 B2 | 1/2015 | Grokop et al. |
| 10,748,075 B2 | 8/2020 | Chowdhary et al. |

(Continued)

FOREIGN PATENT DOCUMENTS

| CN | 103460221 A | 12/2013 |
| CN | 104704863 A | 6/2015 |

(Continued)

OTHER PUBLICATIONS

First Office Action and Search Report for co-pending CN Appl. No. 201810433359.6 dated Mar. 16, 2021 (6 pages).

*Primary Examiner* — John H Le
(74) *Attorney, Agent, or Firm* — Crowe & Dunlevy

(57) ABSTRACT

Motion activity data is collected from at least one sensor. An initial motion activity classifier function is applied to the motion activity data to produce an initial motion activity posteriorgram. Pre-processing and segmenting the motion activity data into windows produces segmented motion activity data from which sensor specific features are extracted. An updated motion activity classifier function is generated from the extracted sensor specific features. Subsequent motion activity data is also collected from the at least one sensor, and the updated motion activity classifier function is applied to the subsequent motion activity data to produce an updated motion activity posteriorgram.

16 Claims, 18 Drawing Sheets

(51) Int. Cl.
*A61B 5/00* (2006.01)
*A61B 5/024* (2006.01)
*A61B 5/11* (2006.01)
*G16H 40/63* (2018.01)
*A61B 5/0245* (2006.01)
*A61B 5/22* (2006.01)
*G16H 50/20* (2018.01)

(52) U.S. Cl.
CPC .......... *A61B 5/6831* (2013.01); *A61B 5/6898* (2013.01); *A61B 5/7267* (2013.01); *G16H 40/63* (2018.01); *A61B 5/0245* (2013.01); *A61B 5/222* (2013.01); *G16H 50/20* (2018.01)

(58) Field of Classification Search
CPC ... A61B 5/6831; A61B 5/6898; A61B 5/7267; G16H 40/63; G16H 50/20
USPC .......................................... 702/127, 141, 150
See application file for complete search history.

(56) References Cited

U.S. PATENT DOCUMENTS

| | | |
|---|---|---|
| 2005/0033200 A1 | 2/2005 | Soehren et al. |
| 2012/0310587 A1 | 12/2012 | Tu et al. |
| 2013/0242120 A1 | 9/2013 | Venkatraman et al. |
| 2014/0100835 A1 | 4/2014 | Majumdar et al. |
| 2014/0207401 A1 | 7/2014 | Sung et al. |
| 2014/0312242 A1 | 10/2014 | Valentino et al. |
| 2015/0081247 A1 | 3/2015 | Valentino et al. |
| 2016/0029943 A1 | 2/2016 | Mizuochi et al. |
| 2017/0188895 A1* | 7/2017 | Nathan ............... A61B 5/1122 |
| 2017/0352240 A1* | 12/2017 | Carlton-Foss ........... A61B 5/11 |

FOREIGN PATENT DOCUMENTS

| | | |
|---|---|---|
| CN | 105320278 A | 2/2016 |
| CN | 105760646 A | 7/2016 |
| CN | 107977074 A | 5/2018 |

* cited by examiner

| Device Carry Position | Generalized classifier | Personalized classifier | | |
|---|---|---|---|---|
| | | Entropy within the range 2.4 and 2.9 | Generalized dataset and personalized data of the motion activities of the target user | Generalized dataset and ten multiples of personalized data of the motion activities of the target user |
| Trouser Pocket | 93.73 | 94.51 | | 95.54 |
| Back Pack | 95.50 | 95.55 | | 95.69 |
| In Hand | 92.77 | 92.94 | | 94.65 |
| Arm Swing | 94.93 | 95.32 | | 96.05 |
| Shirt Pocket | 95.37 | 95.65 | | 95.86 |
| Holster | 92.27 | 92.43 | | 92.76 |
| Shoulder Bag | 94.52 | 94.91 | | 95.47 |
| Total Avg. Accuracy | 94.33 | 94.64 | | 95.20 |

FIG. 9

METHOD FOR GENERATING A PERSONALIZED CLASSIFIER FOR HUMAN MOTION ACTIVITIES OF A MOBILE OR WEARABLE DEVICE USER WITH UNSUPERVISED LEARNING

RELATED APPLICATION

This is a continuation of U.S. patent application Ser. No. 15/600,057, filed on May 19, 2017, the contents of which are incorporated by reference.

TECHNICAL FIELD

This disclosure relates to a method for improving classification accuracy of a mobile or wearable device user's motion activities using a classifier that is personalized, starting from a factory-set generalized classifier, in an unsupervised manner.

BACKGROUND

Mobile, tablet, and wearable devices include embedded MEMS sensors like accelerometers, barometers, gyroscopes, magnetometers, and microphones. These sensors can be used by software executed within the device to determine the human motion activity being performed or undertaken by the user. The detection of such motion activities can be used by software to assist with human-machine interaction. Indeed, motion activity aware devices may minimize or even eliminate the need for human input in certain applications involving motion activities. For example, an application may, if the human user is jogging, automatically and without the need for user input, start playing music and switch on health monitoring applications. Thus, the correct detection of human motion activities may be valuable and commercially desirable, particularly in the domains of ubiquitous computing, human machine interaction, and the internet of things.

Typically, such electronic devices use generalized classification techniques to determine which motion activity, such as walking or jogging, is being performed. These generalized classification techniques are not specific to any one user, and are instead designed to provide acceptable performance for any user. However, each person has a different gait when performing such motion activities, meaning that the generalized classification techniques may be more accurate for certain users than for other users. This is compounded by the large differences in human size, shape, and weight, as sensor output for a jogging motion performed by a tall and heavy individual may be substantially different than sensor output for a jogging motion performed by a short and light individual, for example.

Therefore, to provide for better and more accurate motion activity detection and classification, the development of classification techniques that can take into account the different characteristics of different users is needed.

SUMMARY

A method is for operating an electronic device and includes collecting initial motion activity data from at least one sensor of the electronic device, and generating a initial probabilistic context of the electronic device relative to its surroundings from the initial collected motion activity data using a motion activity classifier function. The collected motion activity data is stored in a training data set, and the motion activity classifier function is updated using the training data set. The method also includes collecting subsequent motion activity data from the at least one sensor of the electronic device, and generating a subsequent probabilistic context of the electronic device relative to its surroundings from the subsequently collected motion activity data using the updated motion activity classifier function.

The method may include generating a data selection confidence measure after generating the initial probabilistic context. The collected motion activity data may be stored in the training data set if the data selection confidence measure is greater than a lower threshold, and the collection motion activity data may not be stored in the training data set if the data selection confidence measure is less than the lower threshold.

The collected motion activity data may be stored in the training data set if the data selection confidence measure is greater than or equal to a lower threshold and less than or equal to an upper threshold.

The method may include generating a data selection confidence measure after generating the initial probabilistic context. The collected motion activity data may be stored in the training data set if the data selection confidence measure is less than an upper threshold, and the collection motion activity data is not stored in the training data set if the data selection confidence measure is greater than the upper threshold.

The method may also include determining whether the training data set contains sufficient data prior to updating the motion activity classifier function using the training data set, and not updating the motion activity classifier function unless the training data set contains sufficient data.

The method may additionally include storing the subsequent motion activity data in the training data set, further updating the updated motion activity classifier function using the training data set, collecting further motion activity data from the at least one sensor of the electronic device, and generating a further probabilistic context of the electronic device relative to its surroundings from the further motion activity data using the further updated motion activity classifier function.

The data selection confidence measure may be based upon conditional entropy of the initial probabilistic context. The initial probabilistic context may include a motion activity posteriorgram encompassing multiple different potential contexts, and the data selection confidence measure may be based upon conditional entropy of the motion activity posteriorgram.

The data selection confidence measure may be based upon a difference between highest and second highest of posterior probabilities of motion activities of the probabilistic context.

The training data set may include generalized data and motion activity data collected from the at least one sensor of the electronic device.

The training data set may consist or consist essentially of motion activity data collected from the at least one sensor of the electronic device.

Also described herein is a sensor chip mounted on a printed circuit board (PCB) and electrically coupled to a system on chip (SOC) mounted on the PCB via at least one conductive trace. The sensor chip includes at least one sensing device and a control circuit. The control circuit is configured to collect initial motion activity data from the at least one sensing device, generate a initial probabilistic context of the printed circuit board relative to its surroundings from the initial collected motion activity data using a motion activity classifier function, store the collected motion activity data in a training data set, update the motion activity classifier function using the training data set, collect subsequent motion activity data from the at least one sensor of the electronic device, and generate a subsequent probabilistic context of the electronic device relative to its surroundings from the subsequently collected motion activity data using the updated motion activity classifier function.

The control circuit may output the initial probabilistic context and subsequent probabilistic context to the SOC.

Also disclosed herein is a method including collecting motion activity data from at least one sensor, applying an initial motion activity classifier function to the motion activity data to produce an initial motion activity posteriorgram, performing pre-processing steps and segmenting the motion activity data into windows to produce segmented motion activity data, extracting sensor specific features from the segmented motion activity data to produce extracted sensor specific features, generating an updated motion activity classifier function from the extracted sensor specific features, collecting subsequent motion activity data from the at least one sensor, and applying the updated motion activity classifier function to the subsequent motion activity data to produce an updated motion activity posteriorgram.

BRIEF DESCRIPTION OF THE DRAWINGS

FIG. 9 is a chart showing a weighted accuracy for different carry positions of the device using a generalized classifier and a personalized classifier trained with data having a conditional entropy greater than a lower threshold and less than an upper threshold.

DETAILED DESCRIPTION

Figure 1A:
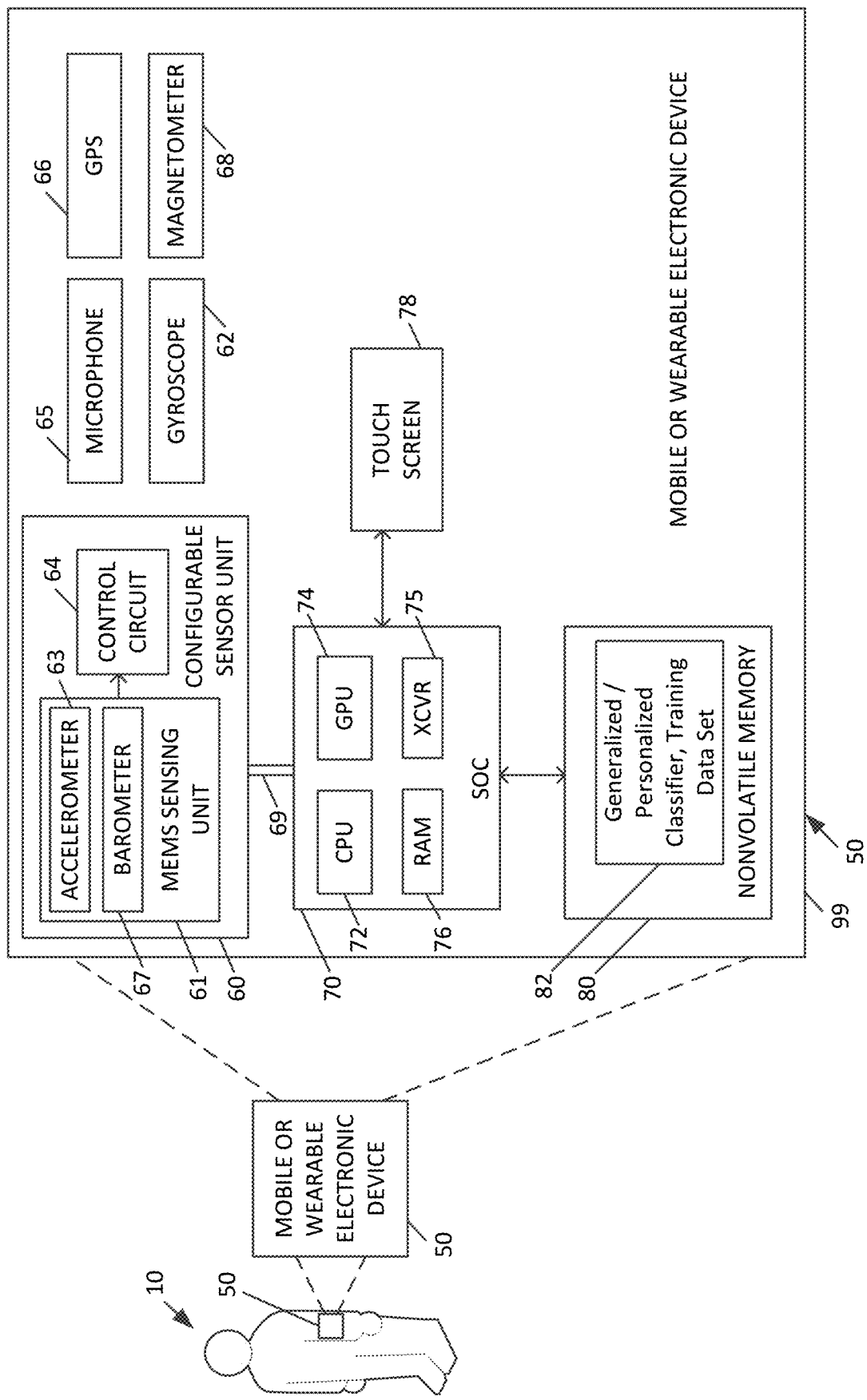
FIG. 1A is a block diagram of a device capable of implementing the methods and techniques described herein in which the personalized classifier is stored in nonvolatile memory.

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout.

Operation in accordance with this disclosure will first be explained in general, and thereafter will be described in greater detail.

Described herein is a computational method for determining a mobile or wearable device user's motion activity with one or more sensors, with the objective of achieving an improved level of accuracy, by inducting samples of motion activity of target user into a factory-set generalized dataset to provide a training data set. The target user's data being inducted in the factory-set generalized dataset is dependent on a data selection measure (DSM) of a posterior probability classifier. The DSM is a measure of confidence in the classifier's detected activity that is based on the posterior probabilities of the different motion activities. Using the training data set, a factory-set generalized posterior probability classifier can be migrated to a personalized posterior probability classifier specific for the target user.

This method allows for flexibility in the range of the DSM based upon which the sample data of motion activities of the target user may be inducted in to training dataset. A computational architecture described herein provides the output of the detected motion activity, through heterogeneous sensor measurements and the personalized classifier. The migration from the factory-set generalized classifier to the target user-specific personalized classifier is effective when a sufficient or significant amount of target user's data within the pre-specified range of the DSM is available.

The personalized classifier may be of two types: either a personalized classifier containing a generalized dataset as well as motion activity labeled data from the target user, or a personalized classifier containing motion activity labeled data from the target user only. The output of the personalized classifier is in the form of the detected motion activity output periodically, and that is derived from the probability of each motion activity class obtained by the classifier, based upon the data collected from the sensor(s).

Motion activities may be detected using one or more of the aforementioned sensors. To sense motion activity, under a supervised learning approach, a generalized dataset or generalized classifier, which may be factory set, may be provided. The generalized dataset includes data from other human subjects that is different from the target user's data, and is used for training the generalized classifier for detecting motion activities.

The pattern of motion activities as recorded on sensor(s) are generally person specific as these depend on height, weight, gender, age of the person, in addition to personal style of performing the activities. The common motion activities that have personalized characteristics are walking, cycling, going upstairs, going downstairs, and jogging. Also, as mobile and wearable devices are personal devices of a user, the option of designing and using a personalized classier is available. As a result, a person dependent classifier trained on the target user's motion activity patterns will detect motion activities more accurately. Even though a target user specific classifier designed using the user's motion activity data would be more accurate, designing a classifier for each target user by explicitly enquiring for the samples of each motion activity from the target user is impractical. Thus, a personalized classifier is sought which does not explicitly request from the user data samples of each motion activity to build the personalized classifier. The personalized classifier may have the advantage of increased accuracy as it would be able to detect and classify according to the target user's motion activity patterns.

With initial reference to FIG. 1A, an electronic device 50 upon which the various techniques and methods of this disclosure may be performed is now described. The electronic device 50 may be a smartphone, tablet, smartwatch, or other wearable device that is carried by, or worn by, a user 10. The electronic device 50 includes a printed circuit board (PCB) 99 having various components mounted thereon. Conductive traces 69 printed on the PCB 99 serve to electrically couple the various components together in a desired fashion.

A system on chip (SOC) 70, which comprises a central processing unit (CPU) 72 coupled to a graphics processing unit (GPU) 74, is mounted on the PCB 99. Also coupled to the CPU 72 is random access memory (RAM) 76 and a transceiver (XCVR) 75 via which the SOC 70 can communicate with remote servers over the Internet. A touch sensitive display 78 is coupled to the SOC 70, and is used by the SOC 70 to display output and receive input. A variety of sensors are coupled to the SOC 70, including a magnetometer 68 used to determine the orientation of the electronic device 50 with respect to the magnetic field of the Earth, a gyroscope 62 used to determining an orientation of the electronic device 50 with respect to the environment, and a microphone 65 used to detect audible noises in the environment. A configurable sensor unit 60 is mounted on the PCB 99 spaced apart from the SOC 70, and coupled thereto by the conductive traces 69. For illustrative purposes only, for example, the configurable sensor unit 70 includes an accelerometer 63 and/or barometer 67 packaged in a MEMS sensing unit 61 and coupled to a control circuit 62. The accelerometer 63 is used for determining accelerations experienced by the electronic device 50, and the barometer 67 used to determine the air pressure in the environment (and thus, the altitude of the electronic device 50).

It should be understood that any now existing or future developed type of sensors could be used with this disclosure, the scope of which is not limited by the type of configurable sensors used. The configurable sensor unit 60 may be formed from discrete components and/or integrated components and/or a combination of discrete components and integrated components, and may be formed as a package.

As illustrated in FIG. 1A as an example, the configurable sensor unit 60 is not a portion of the SOC 70, and is a separate and distinct component from the SOC 70. The sensor unit 60 and the SOC 70 are separate, distinct, mutually exclusive chips mounted on the PCB 99 at different locations and coupled together via the conductive traces 69. It should be understood that this example configuration is just one optional configuration and SOC 70 and the features thereof could be integrated with the sensor unit 60 in some cases, which is also included in the scope of this disclosure.

In operation, the SOC 70 may acquire data from the various sensors 62, 63, 65, 66, 67, 68 at an acquisition rate, and may process the data so as to determine a context of the electronic device 50 relative to its environment. Contexts will be explained in detail.

In operation, the control circuit 64 acquires data from the accelerometer 63 and/or the gyroscope 62, and processes the data so as to generate a context of the electronic device 50 relative to its surroundings. This processing is performed by the control circuit 64 using a processing technique operating in accordance with programmable configuration data. The processed data is then output by the control circuit 64 to the SOC 70 for use thereby.

The context of the electronic device 50 may be where on the user's body it is carried (i.e. in pocket, in hand, in holster), a current method of locomotion of the user (i.e. running, walking, driving, bicycling, climbing stairs, riding a train, riding a bus), an orientation of the electronic device 50 with respect to gravity. Another example context may be movement of the electronic device 50 in a gesture, such as a user raising a smartwatch in to a position to view the screen thereof, shaking the electronic device 50, double tapping the touch screen 78 of the electronic device 50, rotating the electronic device 50 either clockwise or counterclockwise, and swiping the touch screen 78 to the left, right, top, or bottom.

Figure 2:
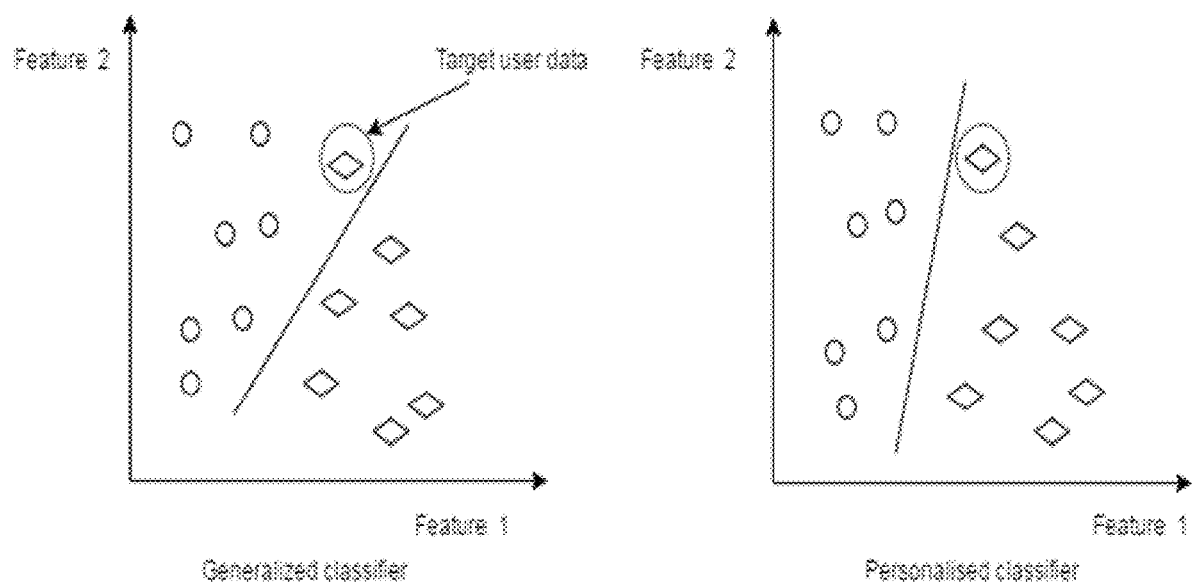
FIG. 2 includes graphs depicting target user data being incorrectly classified with the use of a generalized classifier, and correctly classified with the use of personalized classifier.

Motion activities such as walking, jogging, and the like have characteristic patterns that are user specific and can vary greatly between users. These characteristic patterns be dependent on the height, weight, gender, body proportions (leg length, arm length), and age of the user, in addition to a personal style or gait of performing the motion activities. Mobile and wearable devices 50 tend to be personal to the user and not shared with others. Therefore, it is desirable to generate a personalized classifier that increases the accuracy of motion activity classification. Shown in FIG. 2 is a chart illustrating how the use of a generic classifier may yield inaccurate results, however the use of a personalized classifier instead yields accurate results. As can be seen, when using the generic classifier, a diamond shaped marker (representing an instance of a first class) is incorrectly classified as a second class. However, when using the personalized classifier, this diamond shaped marker is correctly classified as a first class.

Even though a target user specific classifier designed using that user's motion activity data would provide for a high degree of accuracy, generating a specific classifier for each target user by explicitly requesting samples of each motion activity from the target user (i.e. supervised learning) is impractical. Thus, the Inventor has developed a personalized classifier which does not explicitly request data samples of each motion activity from the user to build the personalized classifier. The personalized classifier has the advantage of increased accuracy as it is able to detect and classify according to the target user's specific motion activity patterns.

Figure 3:
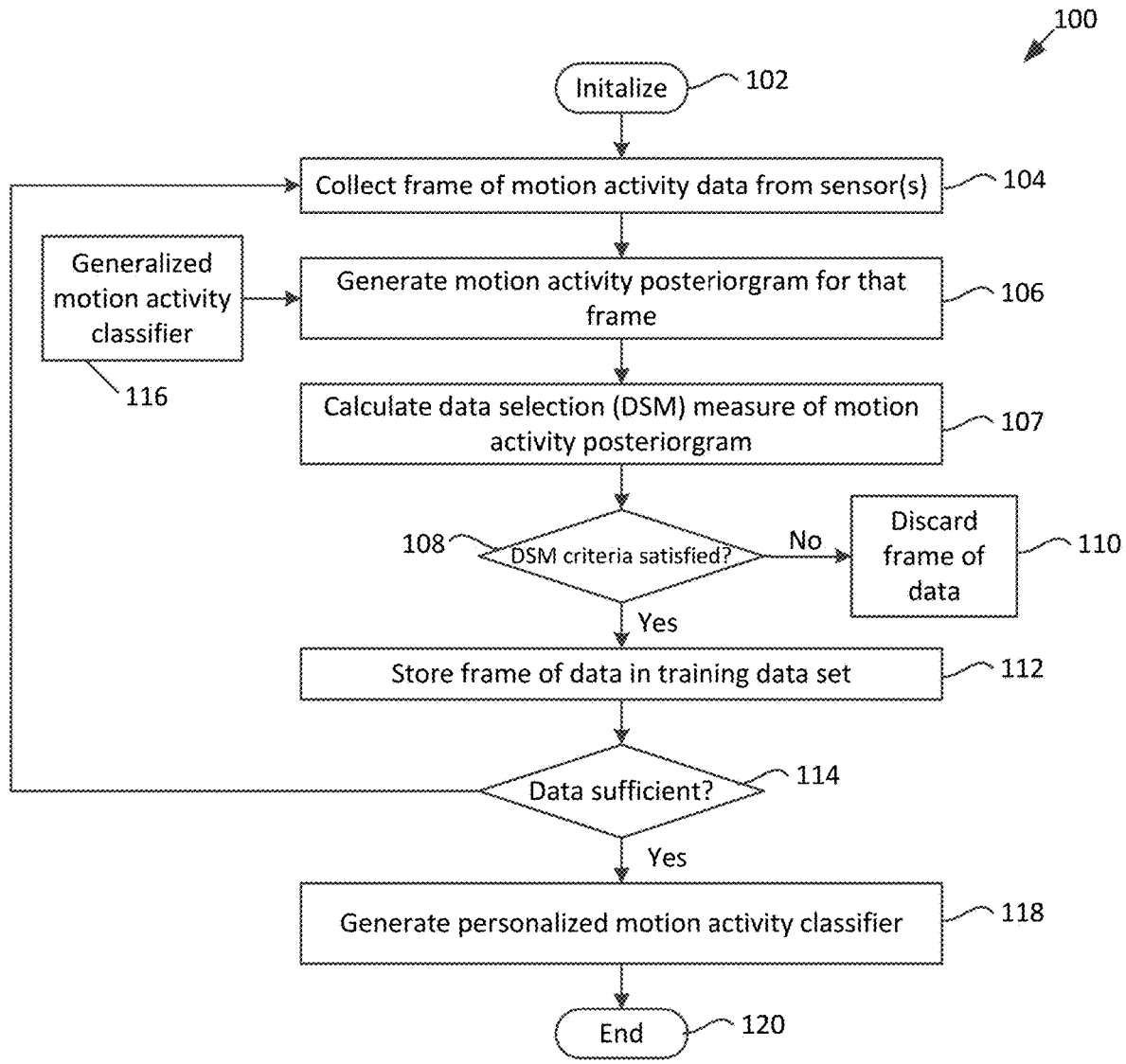
FIG. 3 is a flowchart of a method of generating a personalized classifier of human motion activity of a mobile or wearable device user from a generalized classifier using unsupervised learning.

With reference to FIG. 3, generation of a personalized classifier using unsupervised learning is now described. After initialization of the sensors 62, 63, 65, 66, 67, 68 (Block 102), the control circuit 64 uses one or more of the sensors 62, 63, 65, 66, 67, 68 to collect a frame of motion activity data (Block 104). The control circuit 64 pre-processes the frame of motion activity data (i.e. performs noise filtering, segmenting, and windowing, further details of which will be given below), and then computes the posterior probabilities of the motion activities of that frame (Block 106) using a factory-set generalized classifier (Block 116). The set of these probabilities is called a "posteriorgram".

The generation of the motion activity posteriorgram is independent of the carry position of the electronic device 50 by the user, and can be performed by the control circuit 64 using a suitable machine learning algorithm for generating the posteriorgram like Artificial Neural Network (ANN), Recurrent Neural Network (RNN), Hidden Markov Model (HMM), Support Vector Machine (SVM), etc.

Using the posteriorgram, a Data Selection Measure of the classifier's detected motion activity (confidence level) is calculated by the control circuit 64 (Block 107). The DSM may be calculated using a conditional entropy function, or as a function of a difference between the highest probability and second highest probability in the motion activity posteriorgram, or using any other suitable measure.

If the DSM is within a pre-specified range, then the sensor data of the target user that was used to calculate the posteriorgram is inducted by the control circuit 64 into a training database (Block 112). If the DSM is outside of that range, the control circuit 64 discards the sensor data (Block 110).

The threshold or threshold used may be of three types. First, the threshold could be a lower threshold ($T_L$) such that target user data having a DSM higher than the threshold will be stored in the training database for use with the personalized classifier training. Second, the threshold could be an upper threshold ($T_U$) such that target user data having a DSM lower than the threshold will be stored in the training database for use with the personalized classifier training. In the third case, the thresholds could be a range having a lower threshold ($T_L$) and upper threshold ($T_U$) and target user data having a DSM in the specified range will be stored for use with the personalized classifier training.

Figure 1B:
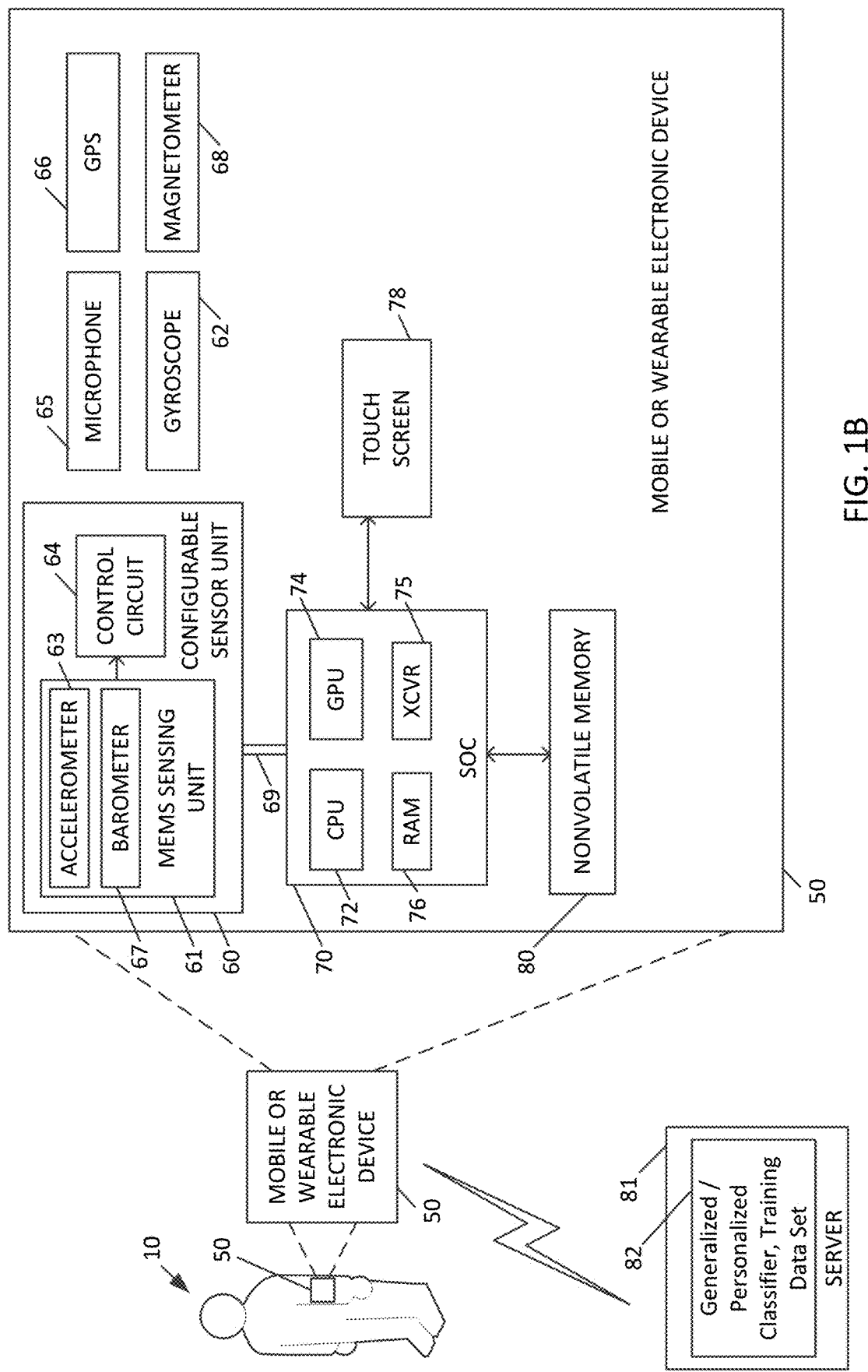
FIG. 1B is a block diagram of a device capable of implementing the methods and techniques described herein in which the personalized classifier is stored on an external server.

As shown in FIG. 1A, the training database 82 may be stored in nonvolatile memory 80 in the electronic device 50. In some cases, such as that shown in FIG. 1B, the training database 82 may be stored on an external server 81. The training database 82 may include only the collected data, or in some cases may also include factory-set generic data.

If there is now a sufficient amount of training data (Block 114), then a personalized motion activity classifier is generated from the training data (Block 118). The personalized motion activity classifier may be generated from only training data collected by the sensors 62, 63, 65, 66, 67, 68, or from a combination of that training data and factory-set generic data. The personalized motion activity classifier may be calculated from scratch, or may be calculated by modifying a factory-set generalized motion activity classifier. If there is not yet sufficient training data to generate the personalized motion activity classifier, the functions of Block 218 are not performed.

Figure 4:
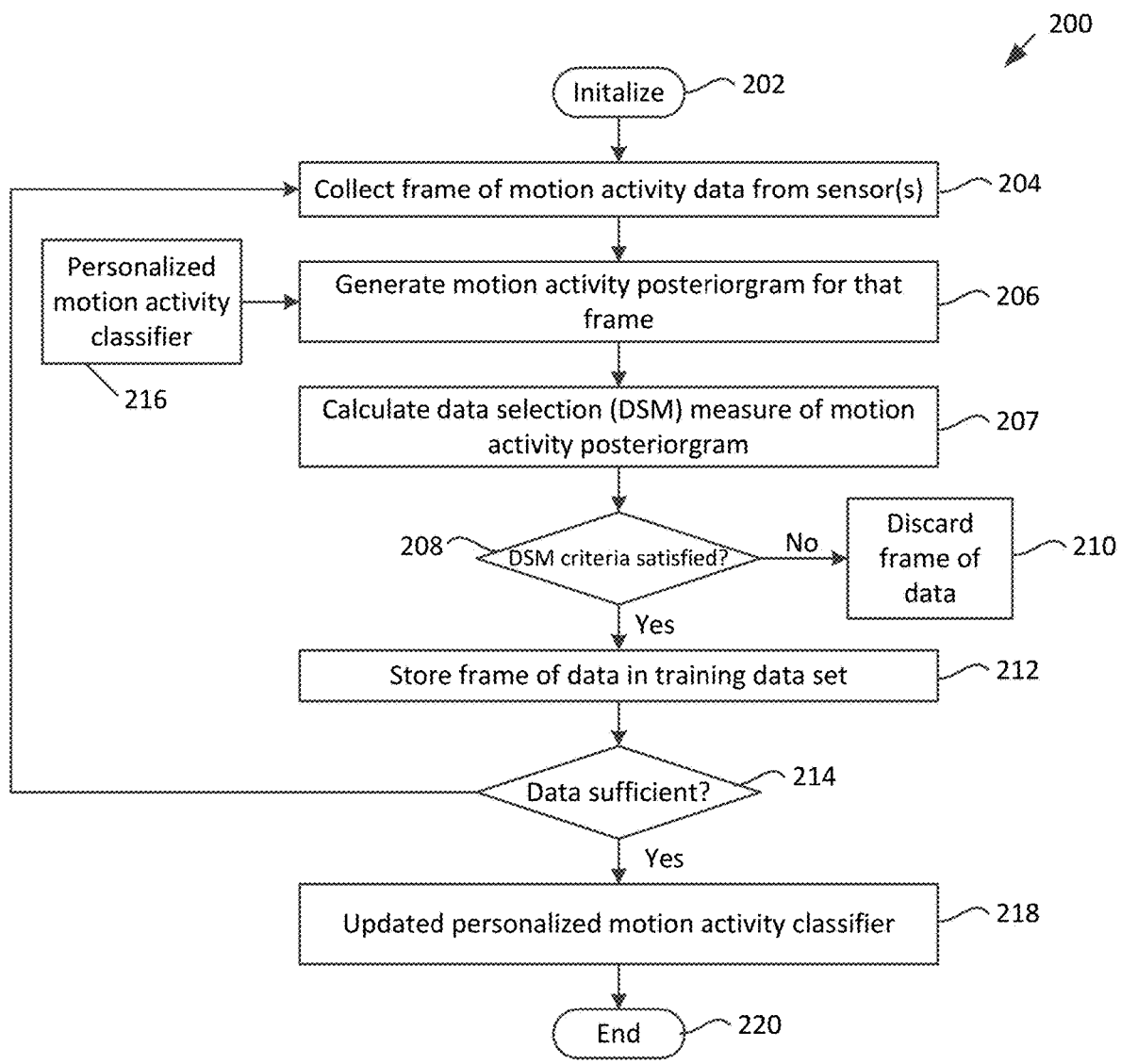
FIG. 4 is a flowchart of a method for iteratively generating a personalized classifier of human motion activity of a mobile or wearable device user from a previous personalized classifier using unsupervised learning.

The personalized motion activity classifier, if calculated, may then be used in the calculation of the motion activity posteriorgram for subsequently acquired frames of data, as will be described with reference to FIG. 4.

The processing of the next frame of motion activity data collected from the sensors 62, 63, 65, 66, 67, 68 by the control circuit 64 proceeds as described above, beginning with initialization (Block 202), proceeding to motion activity collection (Block 204), and then motion activity posteriorgram generation (Block 206). Here, the motion activity posteriorgram is calculated using the personalized motion classifier (Block 216). The processing proceeds as described above with the DSM calculation (Block 207), threshold determination (Block 208), storage of the data in the training data set (Block 212), and the data sufficiency check (Block 214). Here, if there is sufficient training data to update the personalized motion activity classifier, then the personalized motion activity classifier is updated (Block 218).

Consequently, it should be understood that this way, the personalized motion activity classifier is iteratively trained from a previously trained personalized classifier, in an unsupervised learning fashion. The thresholds at any $n^{th}$ iteration may be adaptive and thus may or may not be equal to the thresholds used for generation of the personalized classifier during a previous iteration.

Details of the calculation of the motion activity posteriorgram described above, or any calculations, vectors, or posteriorgrams calculated above, may be found in copending U.S. patent application Ser. No. 15/074,188 (hereby incorporated by reference).

Figure 5:
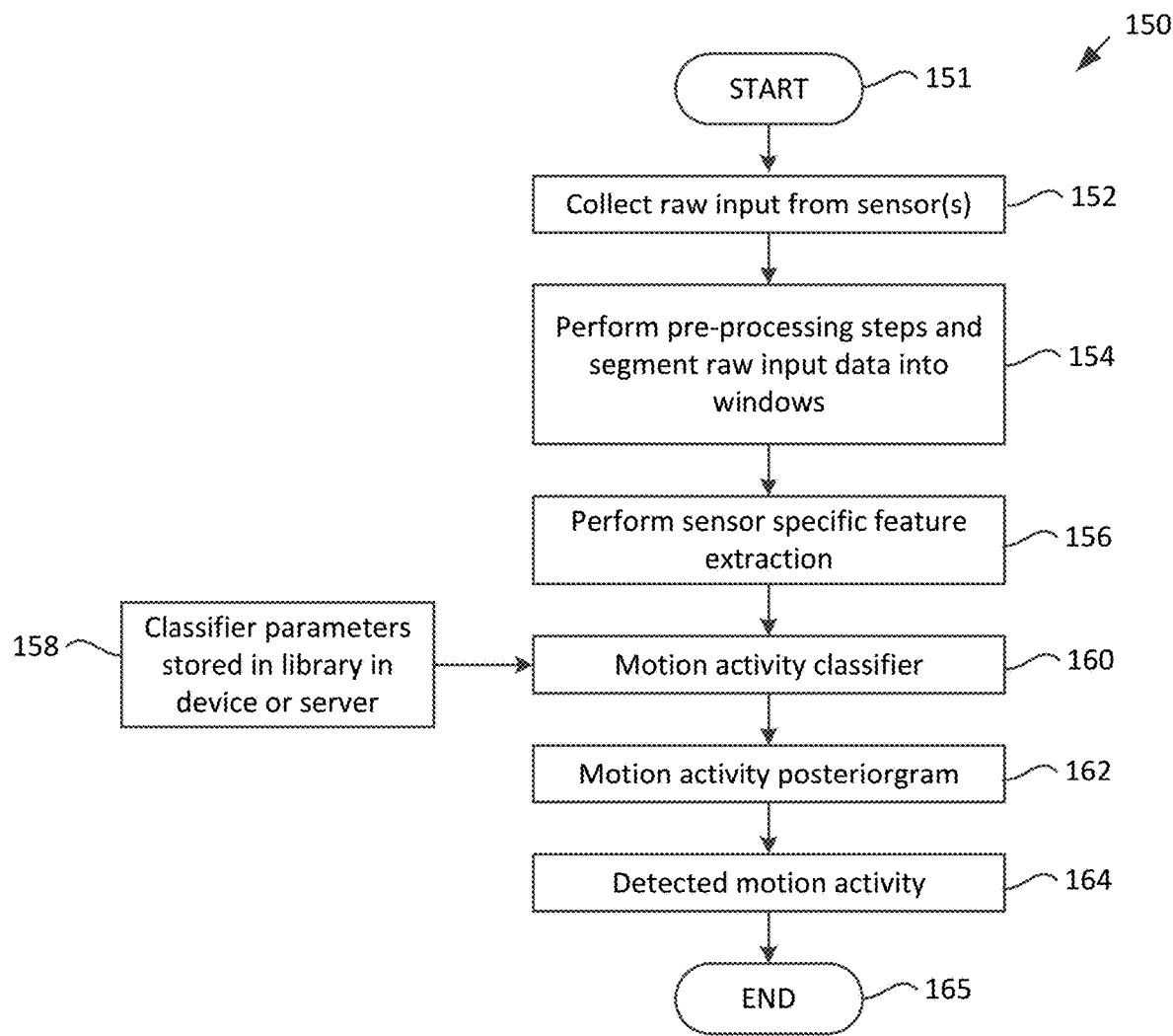
FIG. 5 is a flowchart showing details of the generation of the motion activity posteriorgram and detection of motion activity in FIGS. 3-4.

Depicted in FIG. 5 is a flowchart 150 describing techniques for determining the posterior probabilities for a particular set of human motion activities from data obtained from the sensors 62, 63, 65, 66, 67, 68.

For illustration purposes, consider the motion activity contexts of a user that are grouped in a motion activity vector: Motion Activity Vector (MAV)=[stationary; walking; jogging; going upstairs; going downstairs; elevator up elevator down; bicycling; driving; none of these].

The MAV is a superset of the activities that may be personalized for the target user. The MAV is comprised of nine motion activities of which at least five motion activities (i.e. walking, jogging, cycling, walking upstairs, and walking downstairs) may be personalized. The MAV has one "class" or element in each vector that is possible at a given time i.e., the elements are mutually exclusive and a "none of these" class represents the remaining motion activities that are not explicitly incorporated as elements. This allows the sum total of probability of the mathematically relevant elements of a vector to be equal to one. Also, this makes the motion activity vector representation flexible so that new classes of motion activity can be explicitly incorporated.

The posterior probability of each motion activity given the data from one or more sensors 62, 63, 65, 66, 67, 68 is the corresponding posteriorgram of the MAV. Let it be named as the Motion Activity Posteriorgram (MAP).

Samples of the effectiveness of the above techniques will now be given. Data was used for eleven persons, utilizing seven device carry positions for nine activities. These activities include walking, cycling, stationary, going upstairs, going downstairs, jogging, in-vehicle, elevator up, and elevator down. The user may carry the device 50 in various body positions, such as in a trouser pocket, in a backpack, in-hand, in an arm swinging, in a shirt pocket, holstered, and in a shoulder bag, which are used for the data to be presented. Thus, the data used has wide diversity.

After raw motion activity data is collected from the sensors 62, 63, 65, 66, 67, 68 the control circuit 64 performs pre-processing (Block 154) and segments the data into windows. The pre-processing steps are as follows. The sampling frequency of the accelerometer 63 is 50 Hz, which is downsampled to 20 Hz. The sampling frequency of the barometer is 67 is 20 Hz. The window size is taken as five seconds with a three second overlap. Hence, the motion activity classifier is capable of providing a detected motion activity decision every two seconds.

Several time domain and frequency domain features are calculated for each frame. The time domain features from the accelerometer are mean, maxima, minima, zero crossing rate (ZCR), $10^{th}$ order linear prediction coefficients (LPC), root mean square (RMS) of the accelerometer magnitude, and three cumulative plot features. To derive the cumulative plot features, sorted time domain samples of each windowed frame are taken. From the sorted time domain data, the following mean are calculated from the specified data range:
1. Mean Minima: is defined as the mean of first 15% of the sorted data of the frame.
2. Mean Middle: is defined as the mean of the sorted data of the frame from 30% to 40%.
3. Mean Maxima: is defined as the mean of the sorted data of the frame from 80% to 95%.

The frequency domain features from the accelerometer 63 are forty nine DFT coefficients, maxima of the DFT magnitude, frequency of maximum DFT magnitude bin, and energy in six frequency bands where the bands are as follows: Band 1: 0.2-1 Hz, Band 2: 1-2 Hz, Band 3: 2-3 Hz, Band 4: 3-4 Hz, Band 5: 4-5 Hz, and Band 6: 5-7 Hz.

A total of seventeen features in the time domain and ten features in the frequency domain are calculated for each windowed frame. There are ten features extracted from the barometer data that are the maxima, minima, RMS, six LPC coefficients, and the slope of the pressure variation in the time window. The above set of features per frame of data from the accelerometer 63 and barometer 67 are used to model a probabilistic machine learning algorithm.

Several machine learning algorithms for classification like ANN, HMM, SVM, etc. were implemented, and it was found by the Inventors that a particularly accurate detection is obtained using the SVM. The basic SVM is a non-probabilistic supervised learning algorithm for binary classes. The SVM generates a separating hyperplane such that the width of separation is the maximum. There are several methods that extend SVM for multiclass classification such as maximum wins voting (MWV), winner takes all (WTA), and directed acyclic graph (DAG). The approach used in the classifier below is a soft-decision SVM with DAG. DAG is comprised of several binary classifiers in a tree structure that solves the multiclass classification problem. For M classes of motion activities, there are 0.5*M (M−1) number of binary classifiers between pairs of classes that are used. Each binary classifier in the DAG is trained to classify between a pair of classes. Finally, motion activity posteriorgram for 9 motion activity classes is obtained by normalizing the probabilities obtained from binary classifiers.

SVMs can use linear as well as nonlinear partitions for classification. A kernel function is used for non-linear classification, and transforms the features into a higher dimensional space in which they are linearly separable with the maximum possible margin. To obtain probabilistic output, the SVM is fit into a sigmoid model with two parameters that are obtained using maximum likelihood estimation from the training data set ($f_i$, $y_i$), where $f_i$ is the set of features from a frame of data and is the corresponding labelled class.

Figure 6:
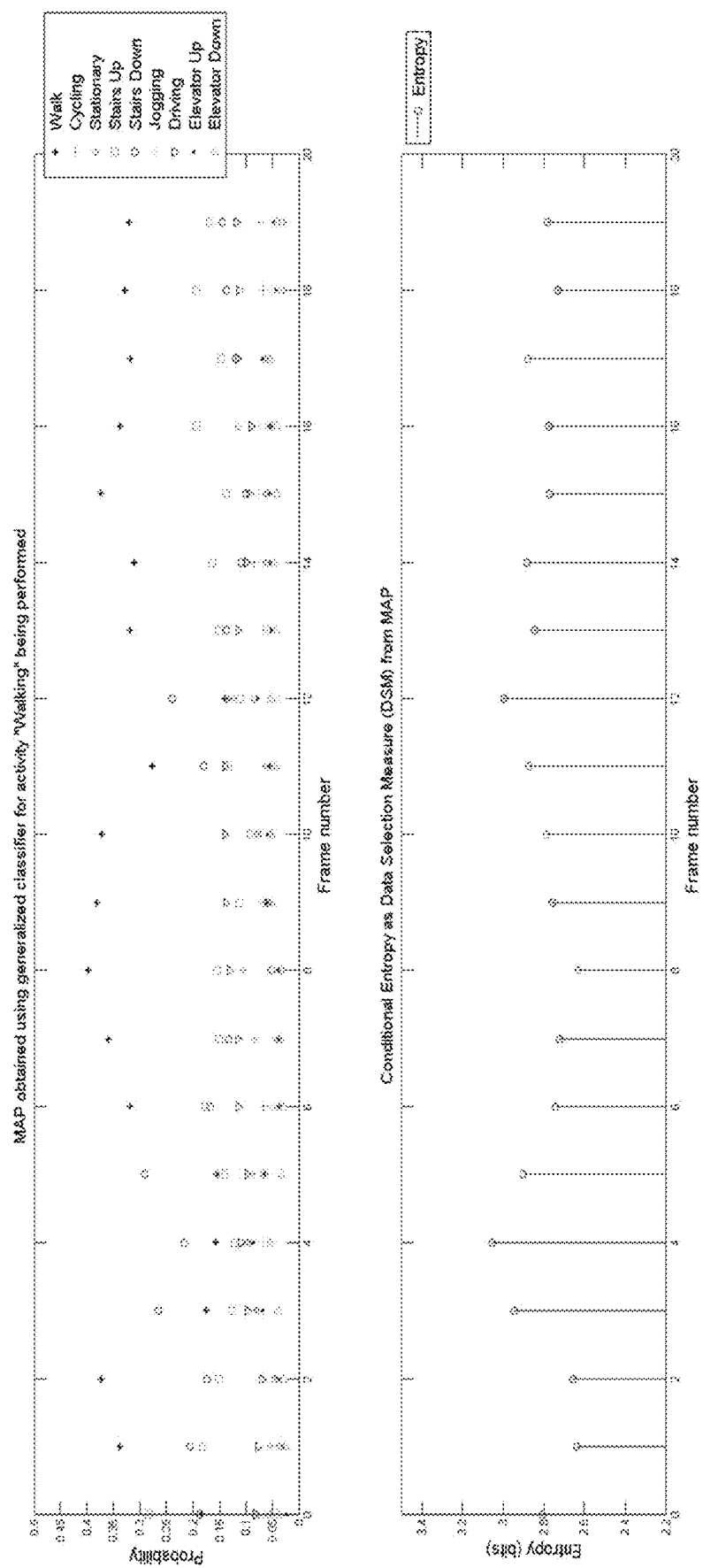
FIG. 6 includes graphs showing posterior probabilities for the motion activity classes in the form of a motion activity posteriorgram (MAP) as a function of frames, and conditional entropy being used for a DSM determined from the MAP for the activity "walking".

FIG. 6 shows the motion activity posteriorgram (MAP) as a function of frames, and conditional entropy as the DSM from the MAP for the activity "walking" when the generalized classifier is used for motion activity detection. The activity "walking" is being performed when the device 50 is in the "arm swing" position. The DSM of the detected motion activity is evaluated based on the conditional entropy function. The second subplot in the figure shows the conditional entropy as a function of each time windowed frame.

Figure 7:
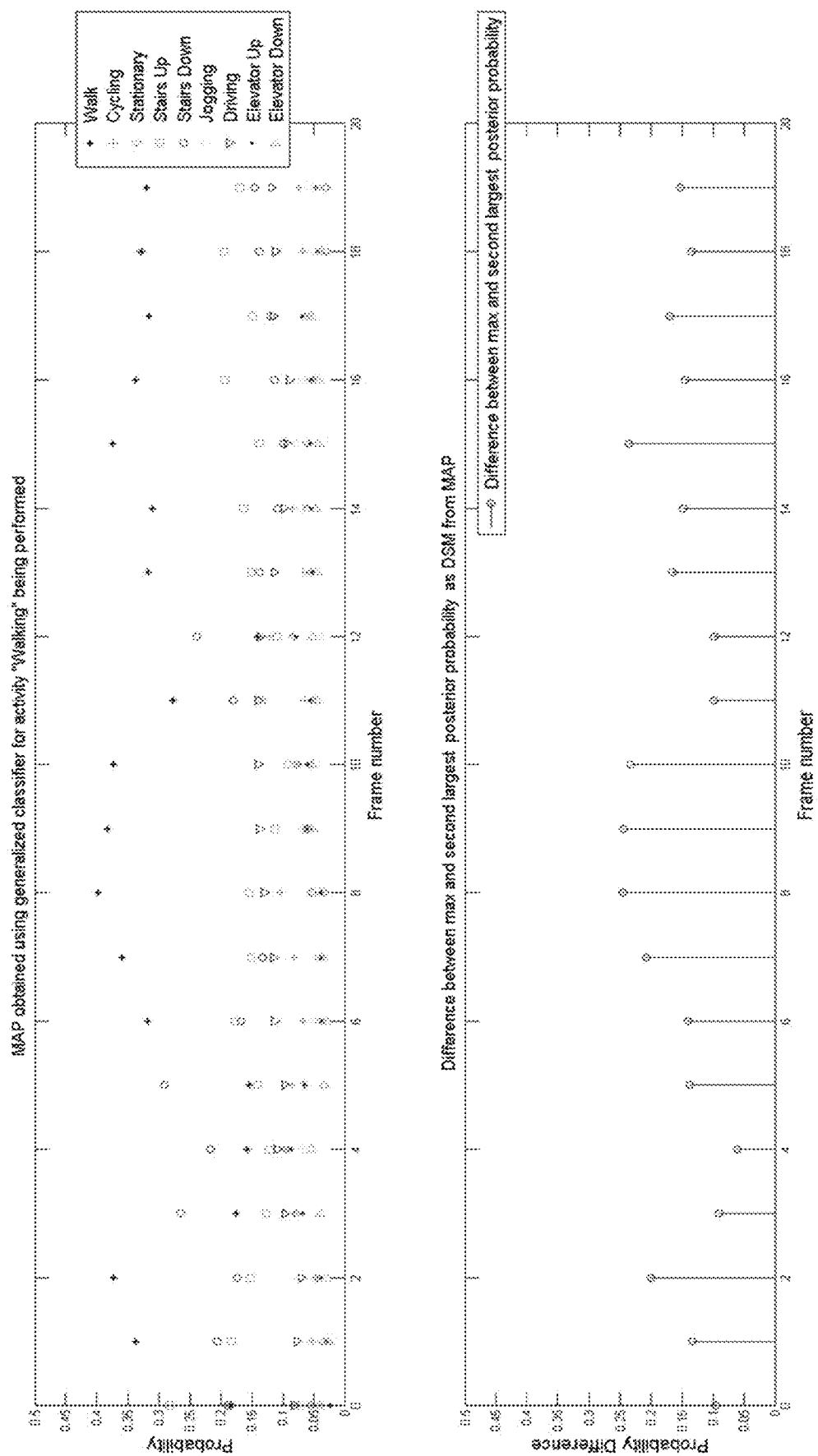
FIG. 7 includes graphs showing posterior probabilities for the motion activity classes in the form of a MAP as a function of frames, and a difference between the highest and second highest posterior probabilities being used for the DSM determined from the MAP for the activity "walking".

FIG. 7 shows the MAP as a function of frames, and using the difference between the largest and second largest posterior probability as the DSM from the MAP for the activity "walking".

Figure 8:
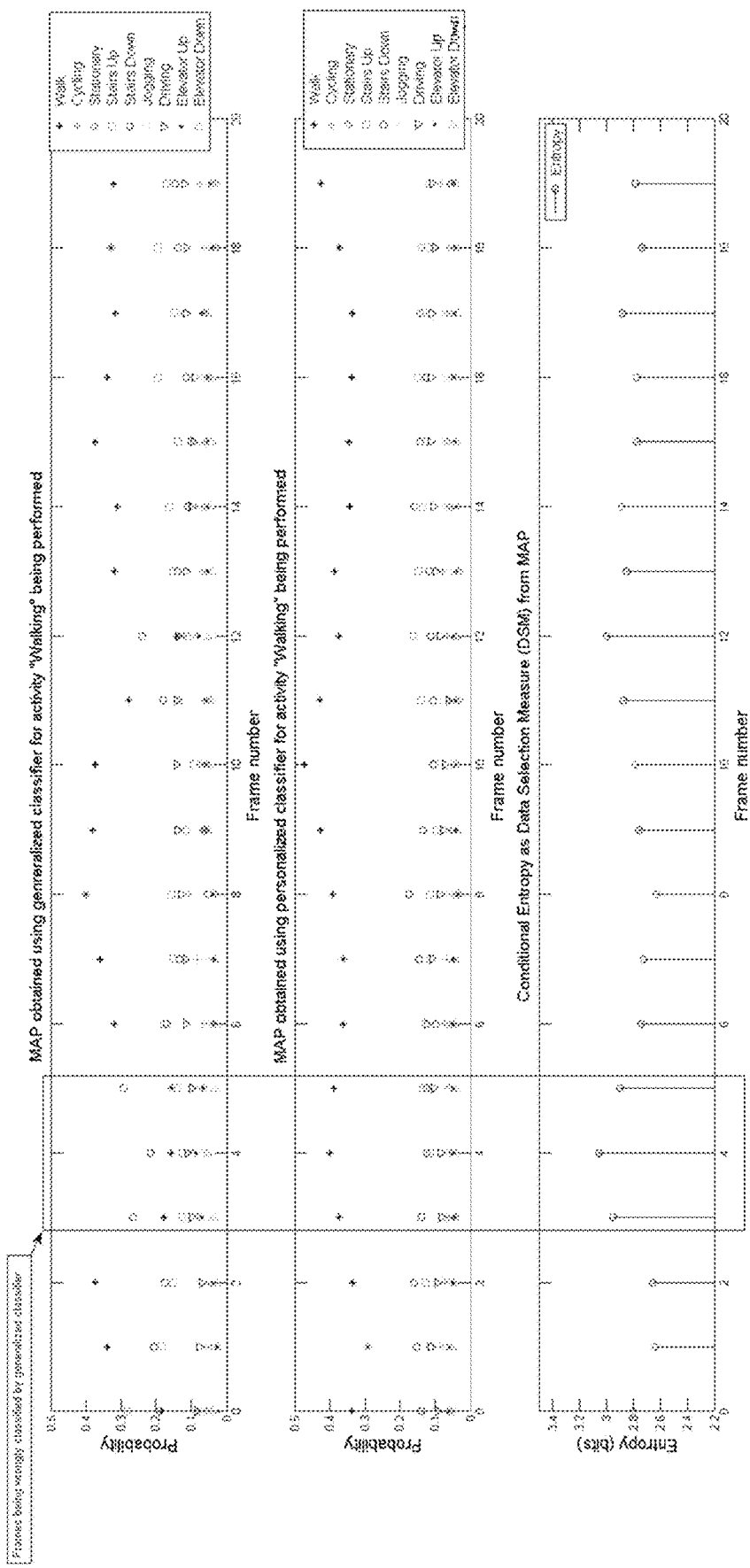
FIG. 8 includes graphs showing a MAP obtained using a generalized classifier with the activity "walking" being performed, a conditional entropy calculated as a measure of the DSM, and a MAP obtained using personalized classifier with the activity "walking" being performed.

In FIG. 8, the conditional entropy (third subplot) which is calculated based on the MAP obtained from the generalized classifier (first subplot) forms the basis of measuring the DSM. The range specified for conditional entropy is 2.4 bits to 2.9 bits.

The data from the accelerometer 63 and barometer 67 which resulted in the conditional entropy in a pre-specified range is saved and further used to update the generalized dataset and form the personalized dataset. As explained above, using the personalized dataset, the classifier is again retrained and a personalized classifier is obtained. The second subplot displays the improvement in the MAP after the induction of personalized data in training of the classifier. For example, a MAP of 80 frames is considered for which the motion activities were detected using the generalized classifier. Out of the 80 frames, 65 frames are correctly classified as the activity "walking". After personalized data of the target user has been used in retraining the classifier, 71 frames out of 80 frames are correctly classified. The MAP obtained using a generalized classifier and the corresponding MAP obtained using the personalized classifier are shown for a section of the 80 frames in the first subplot and second subplot respectively. This illustrates that a personalized classifier improves the detection accuracy of the motion activity class. For this example, as the personalized data in the given confidence range is less compared to the generalized data for the corresponding activity, the personalized data is used ten multiple times.

The target user's data that lies within the pre-specified DSM range is usually less compared to the generalized dataset, so the target user's data is taken in two forms in the personalized dataset, one, in which it is taken once along with the generalized dataset for retraining, and two, in which ten multiple copies of the data are used so that the ratio of the target user's data to generalized data increases. The weighted average accuracy of the nine motion activities in the both the cases are given in FIG. 9. With the personalized dataset for training of the models, the overall weighted average accuracy for nine motion activities increases by 0.87%, which is a reasonable improvement over the high baseline accuracy of the generalized classifier. With the increase in overall weighted average accuracy for the nine motion activities which are a superset of the motion activities that can be personalized, it is evident that the above methods and techniques improve the overall detection of motion activities.

The data was evaluated using the "leave one out" approach. The aim of the evaluation is to demonstrate the efficacy of the personalized classifier. The results are given for seven device carry positions for each of the eleven users. Out of the nine motion activities for which data was collected, five motion activities are candidates for user personalization (as stated, walking, jogging, cycling, going upstairs, and going downstairs). The remaining motion activities (i.e. stationary, in vehicle, elevator up, and elevator down) are not user dependent and hence were not included for personalization of the classifier. The results shown in FIGS. 10-16 are therefore the weighted average accuracy of five personalized human motion activities while taking the eleven users as the target user one at a time. FIGS. 10-16 show the detected accuracy of the motion activities with the device 50 placed at different carry positions by the user. The motion activities are classified using both accelerometer 63 and barometer 67 data.

The classification accuracy results obtained show that when a correct uncertain data sample of the target user is included in retraining the classifier, it leads to an increase in the weighted average accuracy of detection of human motion activity. This reaffirms that when the data samples of the target user that were previously not included in training the classifier for a particular class are now included, then the weighted average accuracy of detection increases. If the data samples that produce low conditional entropy are included in the personalized training dataset, the classification accuracy after inclusion of such data does not change significantly. As the conditional entropy increases, it leads to an increase in the uncertainty and the probability of the samples being wrongly classified increases. Thus, it may lead to an overall decrease in the weighted average accuracy if the samples which are wrongly classified are included in training samples. By including the target user's data samples with labels that have a degree of certainty which are not part of the generalized dataset and excluding the data samples of the target user that have high uncertainty of the detected activity label, the generalized and personalized classifier accuracy based on the conditional entropy in the pre-specified range is increased.

FIG. 9 compares the personalized classifier's performance with the generalized classifier's performance for different device carry positions. The DSM used is that the conditional entropy lies between 2.4 bits and 2.9 bits that is obtained for each frame from the posterior probabilities of the nine motion activities in the MAV. The increase in weighted average accuracy for the device 50 in the trouser pocket position is 1.81%, for the in-hand position is 1.88%, in the arm swing position is 1.12%, and in the shoulder bag position is 0.95%.

Figure 10:
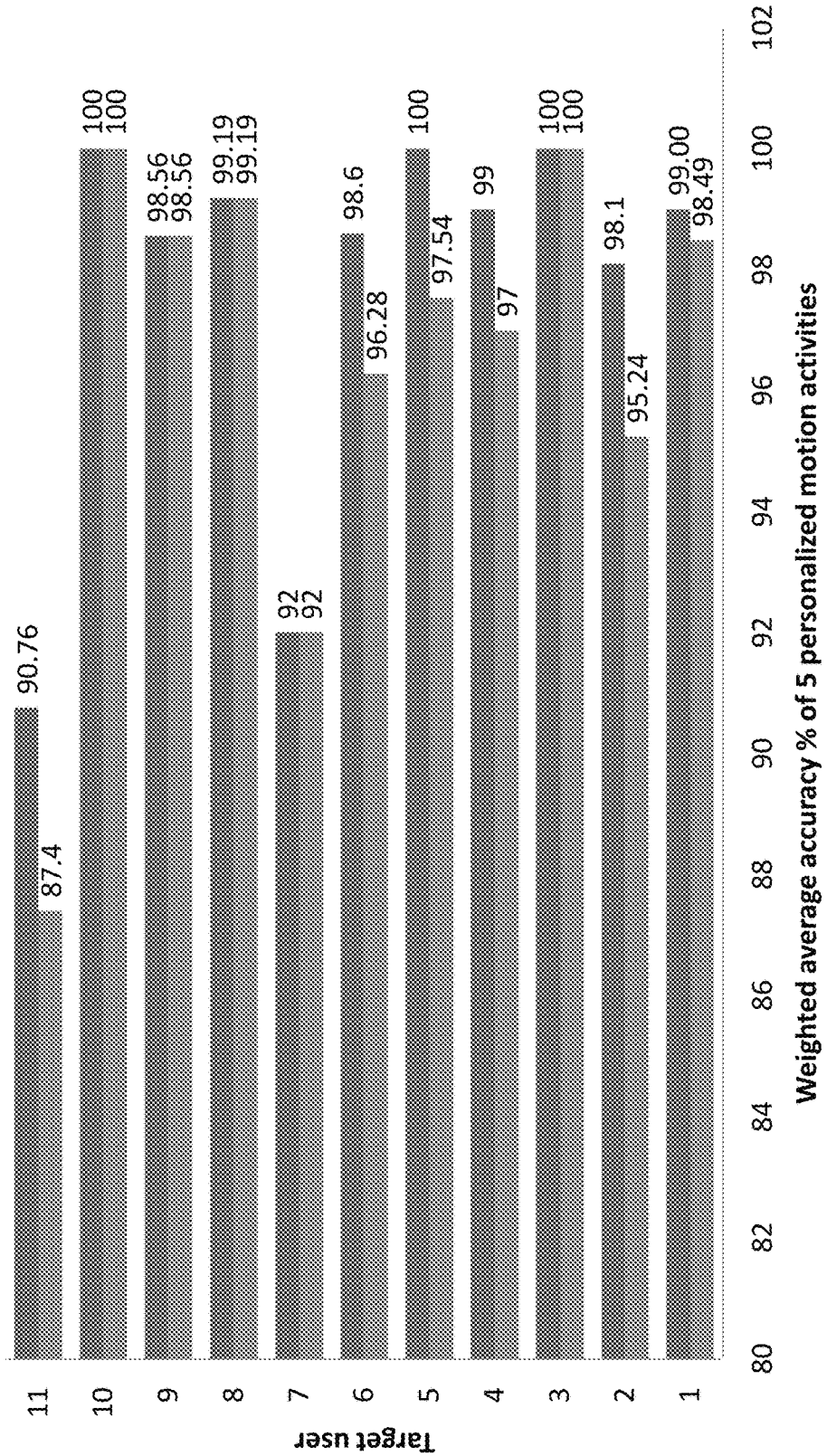
FIG. 10 is a graph showing a weighted average accuracy of personalized and generalized motion activity detection for a device positioned in a trouser pocket.

FIG. 10 shows the weighted average accuracy of five personalized motion activities when the device 50 is placed in the trouser pocket. The target user #11 has the minimum detection accuracy amongst the users when the generalized classifier is used, and it improves markedly from 87.4% to 90.76% after the generalized classifier is transformed to a personalized classifier. Also, the personalized classifier (for each user separately) has caused the weighted average accuracy to increase between 2.0% and 2.86% for target users 2, 4, 5 and 6. There is no significant improvement in the weighted average accuracy of the five personalized motion activities in the case of target users 1, 7, 9 and 10, as they already have a very high classification accuracy with the generalized classifier. Thus it may be observed that when the device 50 is placed in the trouser pocket position, for the target users, the accuracy of detecting the true motion activity increases variously depending on the individual.

Figure 11:
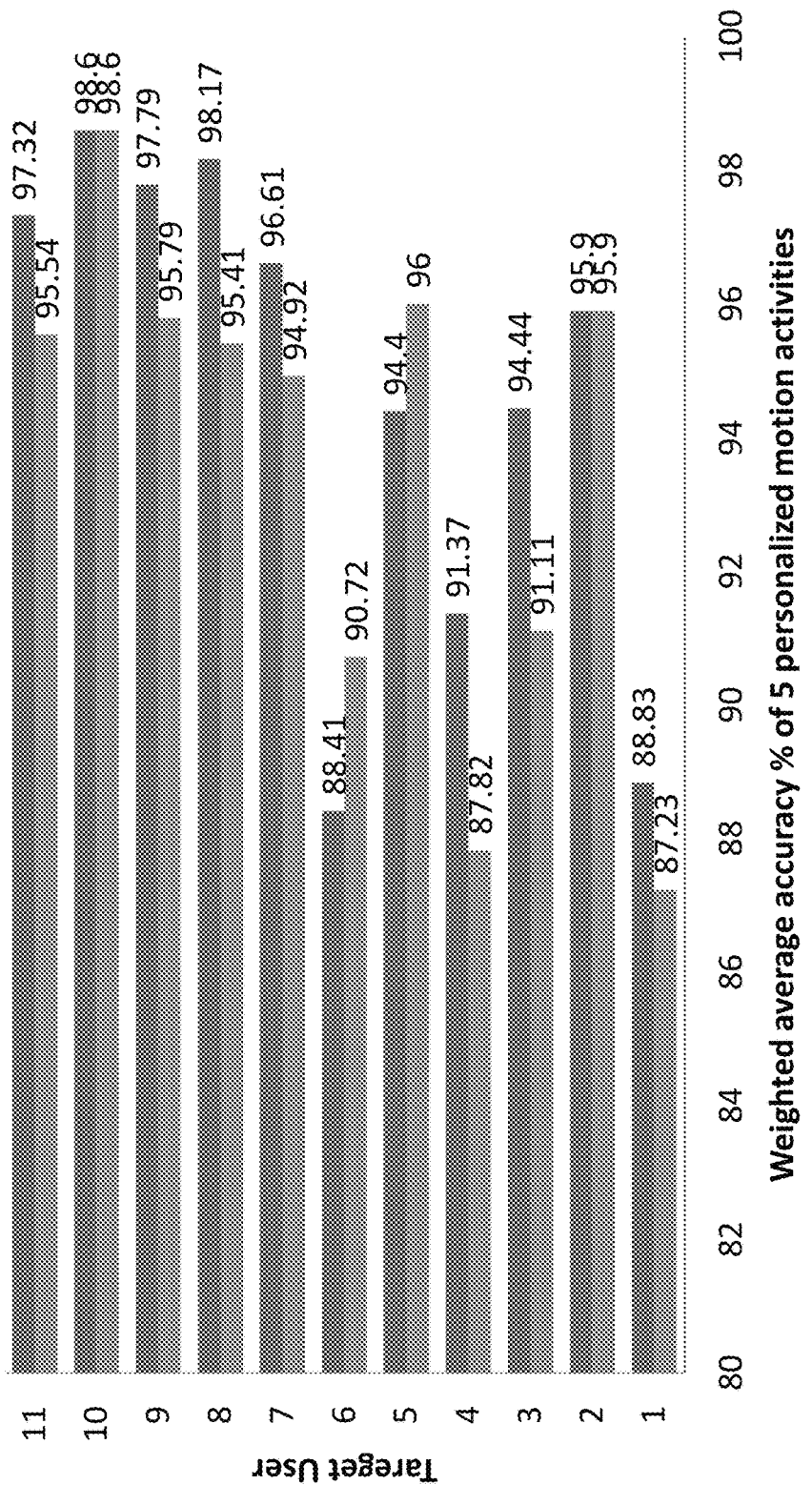
FIG. 11 is a graph showing a weighted average accuracy of personalized and generalized motion activity detection for a device in positioned in a backpack.

FIG. 11 shows the weighted average accuracy of personalized and generalized motion activity classifiers for the device 50 in the backpack position. Target users 1, 3, 4, 7, 8 and 11 have registered significant increases in the weighted average accuracy for the five personalized motion activities. There is a decrease in the accuracy of the personalized classifier for the backpack carry position of the device 50 for users 5 and 6. This may be due to the loose location of the device 50 in the backpack position.

Figure 12:
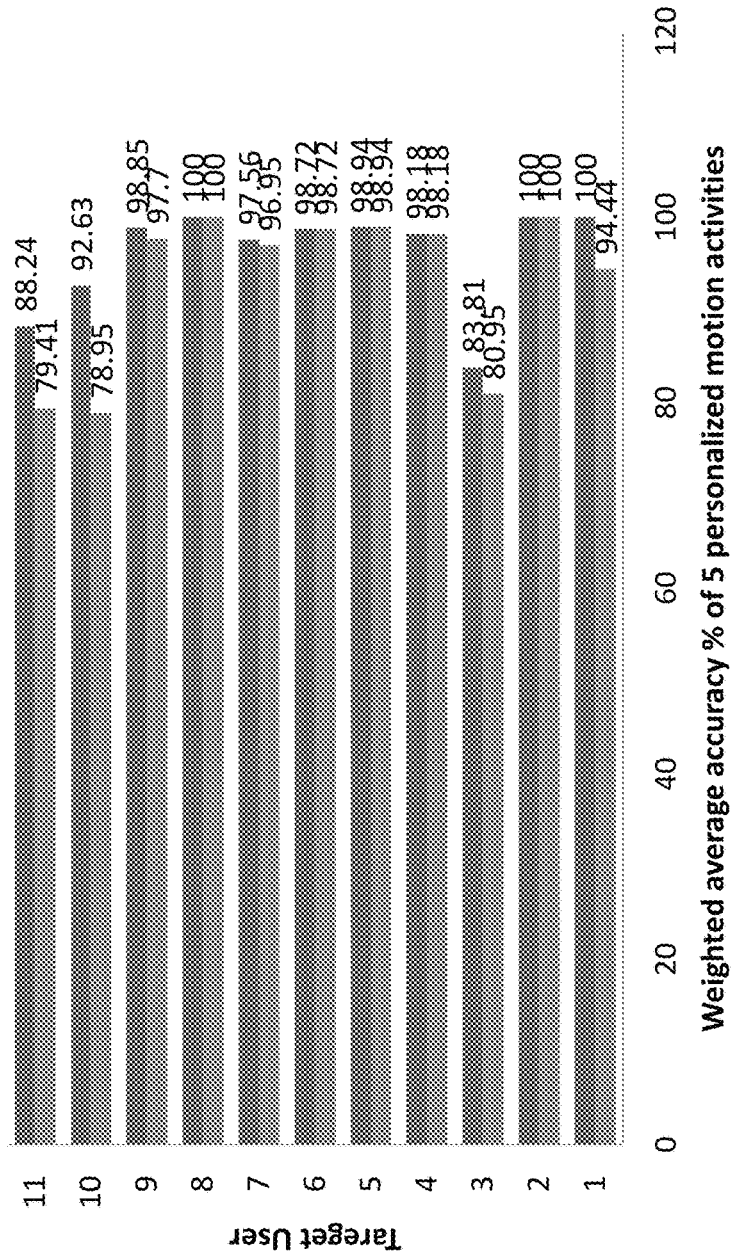
FIG. 12 is a graph showing a weighted average accuracy of personalized and generalized motion activity detection for a device positioned in hand.

FIG. 12 shows the weighted average accuracy of personalized and generalized motion activity for the device 50 in the in-hand position. A particularly useful position for the device 50 when using the personalized model is the in-hand position. When the device 50 is in the in-hand position, there is an improvement in classification accuracy with the personalized classifier for all the target users. Also, there is a large increase in the weighted average accuracy of the five personalized motion activities in the case of users having lower accuracy with the generalized classifier. It can be observed that the target users 3, 10 and 11 who register lower classification accuracy from the generalized classifier register a significant increase with the use of their respective personalized classifiers.

Figure 13:
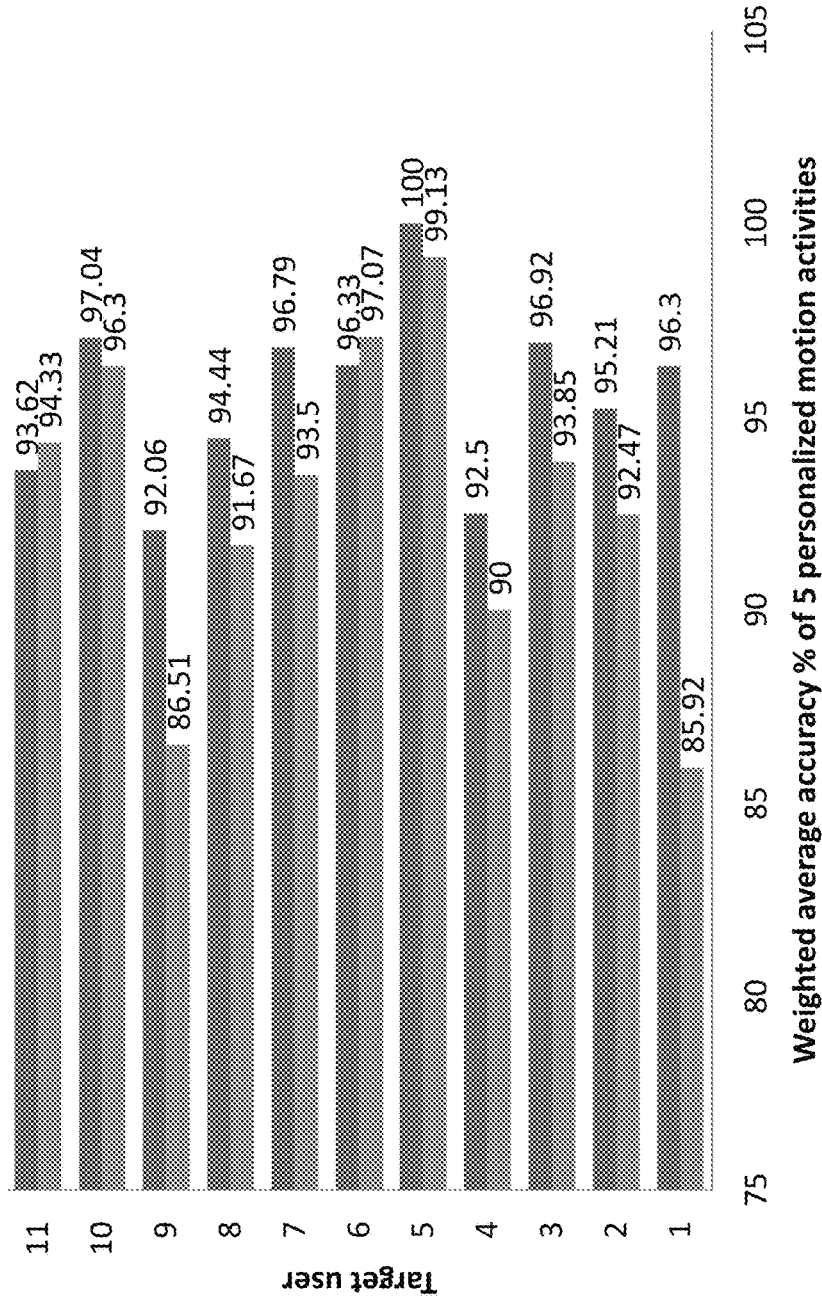
FIG. 13 is a graph showing a weighted average accuracy of personalized and generalized motion activity detection for a device carried by an arm that is swinging.

FIG. 13 shows the weighted average accuracy of the personalized and generalized motion activity classifiers for device 50 in the arm swing position. There is a significant increase of more than 7% in the weighted average accuracy in comparison to the generalized model for the target users having low accuracy, which are users 1 and 9 in this example. The other users also display an increase in the weighted average accuracy except users 6 and 11, for whom there is a slight decrease in the accuracy.

Figure 14:
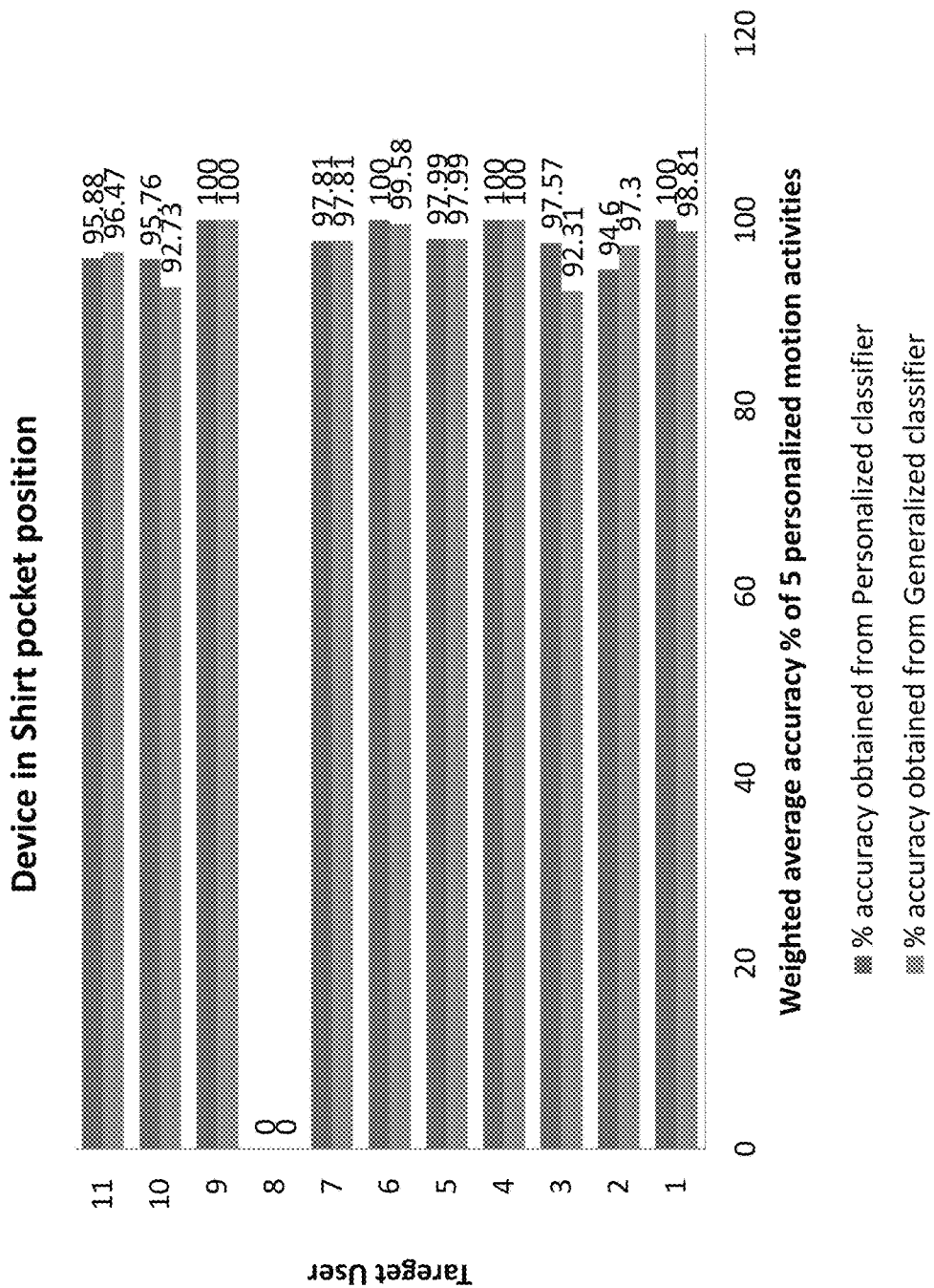
FIG. 14 is a graph showing a weighted average accuracy of personalized and generalized motion activity detection for a device in a shirt pocket.

FIG. 14 shows the weighted average accuracy of the personalized and generalized motion activity classifiers for the device 50 in the shirt pocket position. In this device carry position, except for target user 2, the weighted average accuracy increases (target users 1, 3, 6 and 10) or remains the same (target users 4, 5, 7 and 9). Data was not collected for users 4 and 8 for the device 50 in the shirt pocket position and holster position respectively, thus no corresponding detection result is shown.

Figure 15:
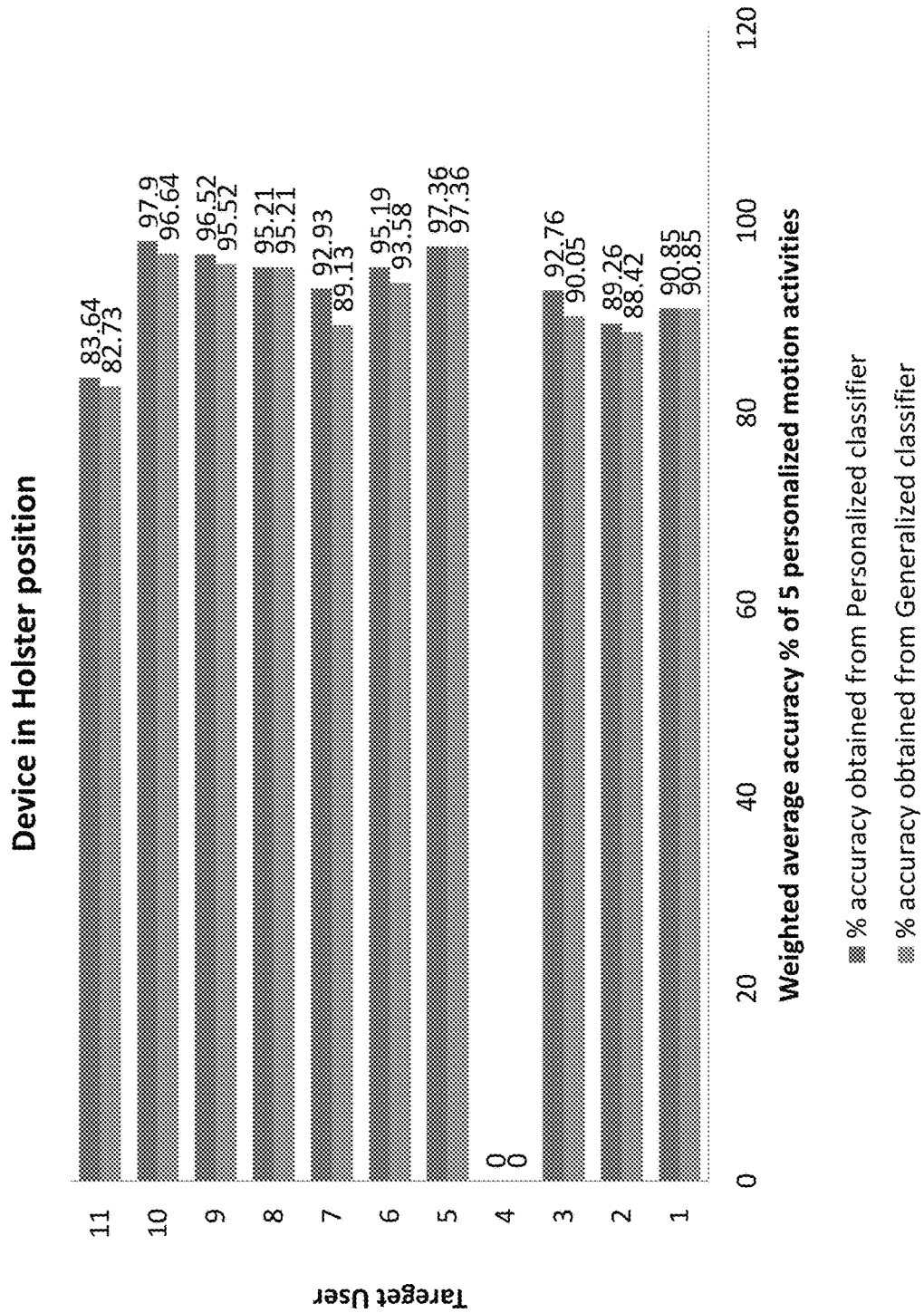
FIG. 15 is a graph showing a weighted average accuracy of personalized and generalized motion activity detection for a device in a holster.

FIG. 15 shows the weighted average accuracy of the personalized and generalized motion activity classifiers for the device 50 in the holster position. The personalized classifier for shows an increase in the weighted average accuracy for the five personalized motion activities for target users 1, 3, 6, 7, 9, and 11, and remains the same for target users 2, 5, 8 and 10. As the device 50 is placed in a tight holster, close to user's body, it rarely decreases the accuracy of motion activity detection.

Figure 16:
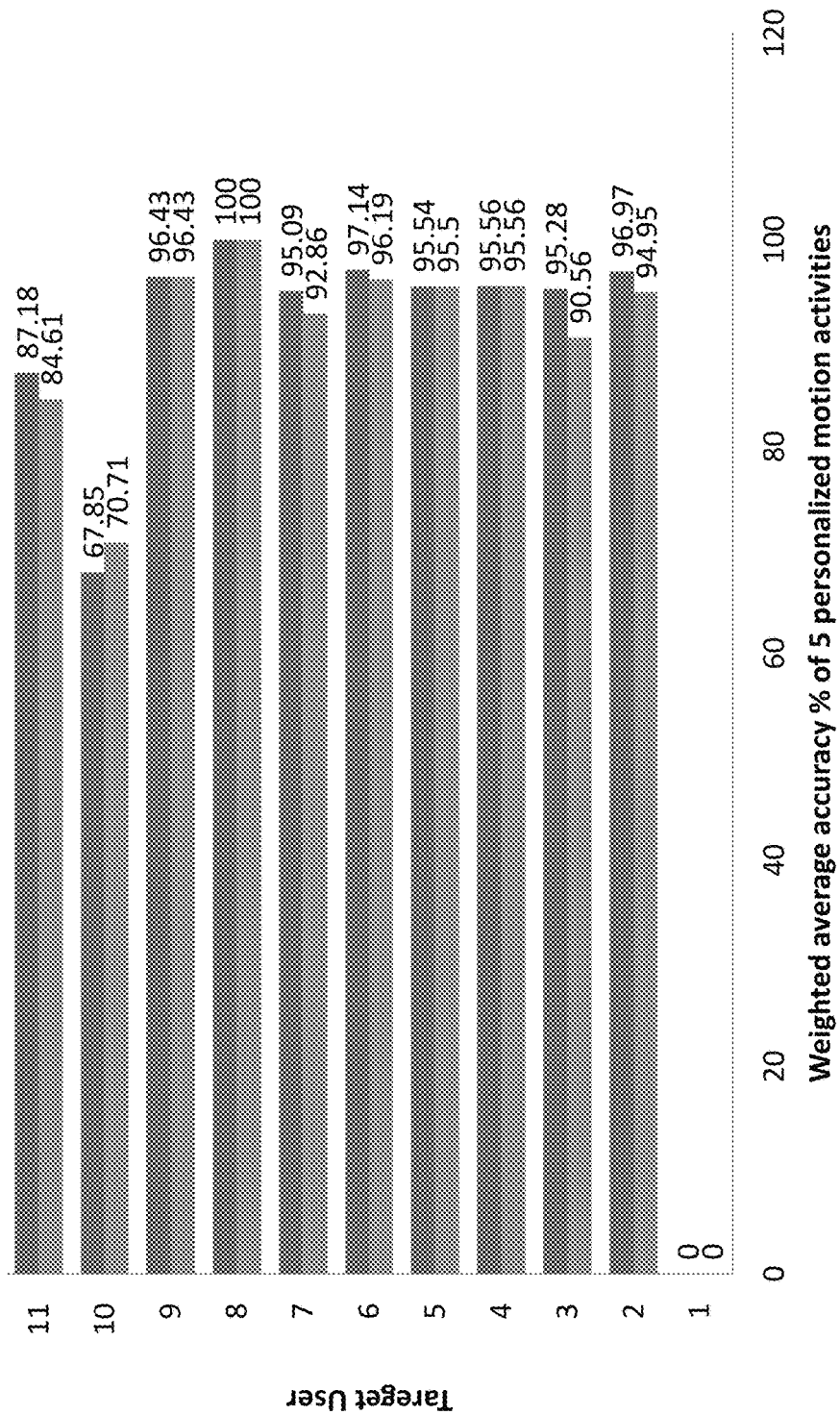
FIG. 16 is a graph showing a weighted average accuracy of personalized and generalized motion activity detection for a device in a shoulder bag.

FIG. 16 shows the weighted average accuracy of the personalized and generalized motion activity classifiers for the device 50 in the shoulder bag position. When the device 50 is in the shoulder bag position, it is generally loosely placed. Thus, personalized patterns are difficult to trace in the recorded data of the respective target users. However, there is an increase in the weighted average accuracy for target user 2, 3, 5, 6, 7 and 11, while for target user 10, the weighted average accuracy has decreased.

It may be seen from the results that the methods and techniques described hereinabove are independent of the device carry position and show overall improvement in weighted average accuracy. Also, the results affirm that the device carry positions which characterize the user's personalized motion patterns in a close manner relative to the device carry positions in which the device 50 is loosely held to body show more improvement in the classification accuracy. The improvement in accuracy of the device carry positions of trouser pocket, in-hand and holster are better than the backpack and shoulder bag carry positions of the device 50. The above figures also emphasize the fact that the method would be relatively more useful for the target user having the gait pattern distinct with respect to gait patterns which are used to train the generalized classifier.

Figure 1C:
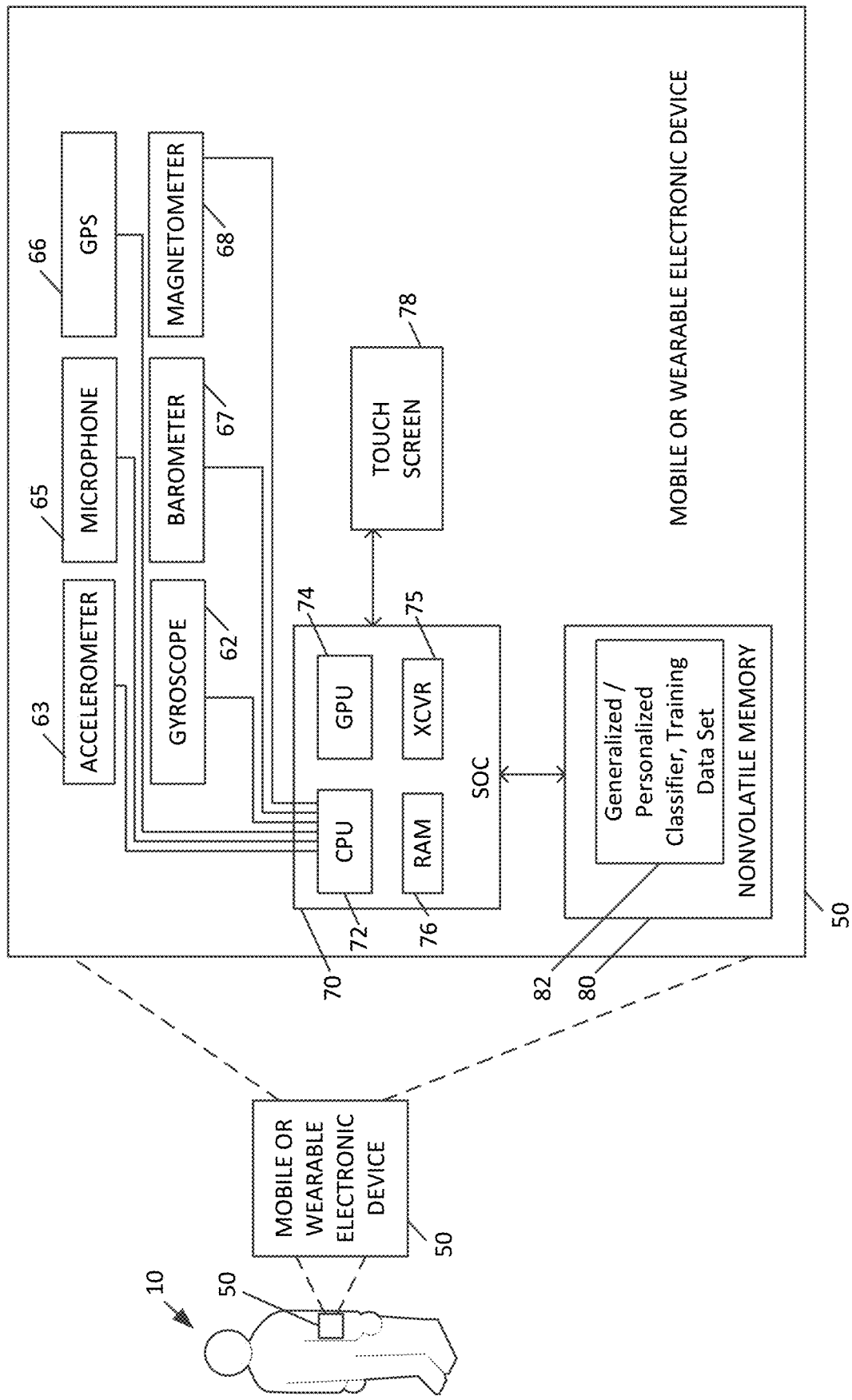
FIG. 1C is a block diagram of an alternative device capable of implementing the methods and techniques described herein in which the personalized classifier is stored in nonvolatile memory.

Although the methods and processing techniques described above have been described with reference to the control circuit 64 performing those actions, in some cases, such as shown in FIG. 1C, the control circuit not be present and instead these actions may be performed by the CPU 72 of the SOC 70. Also, in cases, the control circuit 64 may be present, but the CPU 72 of the SOC 70 may perform these actions. In yet other cases, the control circuit 64 and CPU 72 may each perform different portions of the methods and processing techniques described above.

While the disclosure has been described with respect to a limited number of embodiments, those skilled in the art, having benefit of this disclosure, will appreciate that other embodiments can be envisioned that do not depart from the scope of the disclosure as disclosed herein. Accordingly, the scope of the disclosure shall be limited only by the attached claims.

The invention claimed is:

1. A method, comprising:
    collecting motion activity data from at least one sensor;
    applying an initial motion activity classifier function to the motion activity data to produce an initial motion activity posteriorgram;
    performing pre-processing and segmenting the motion activity data into windows to produce segmented motion activity data;
    extracting sensor specific features from the segmented motion activity data to produce extracted sensor specific features;
    generating an updated motion activity classifier function from the extracted sensor specific features;
    collecting subsequent motion activity data from the at least one sensor; and
    applying the updated motion activity classifier function to the subsequent motion activity data to produce an updated motion activity posteriorgram.

2. The method of claim 1, further comprising:
    storing the collected motion activity data in a training data set; and
    wherein the updated motion activity classifier function is generated based upon the training data set.

3. The method of claim 2, wherein the training data set also includes generalized motion activity data.

4. The method of claim 3, wherein the initial motion activity classifier function is based upon the generalized motion activity data.

5. The method of claim 2, further comprising:
    storing the collected motion activity data in a training data set; and
    wherein the updated motion activity classifier function is generated based upon the training data set.

6. The method of claim 1, wherein the initial motion activity classifier function is based upon generalized motion activity data.

7. The method of claim 1, further comprising:
    generating a data selection confidence measure after generating the initial motion activity posteriorgram;
    wherein the collected motion activity data is stored in a training data set if the data selection confidence measure is less than an upper threshold; and
    wherein the collected motion activity data is not stored in the training data set if the data selection confidence measure is greater than the upper threshold.

8. The method of claim 1, further comprising:
    storing the collected motion activity data in a training data set;
    determining whether the training data set contains sufficient data prior to updating the motion activity classifier function; and
    not updating the motion activity classifier function unless the training data set contains sufficient data.

9. A sensor chip coupled to a system on chip (SOC), the sensor chip comprising:
    at least one sensing device; and
    a control circuit configured to:
        collect motion activity data from at least one sensor of the at least one sensing device;
        apply an initial motion activity classifier function to the motion activity data to produce an initial motion activity posteriorgram;
        perform pre-processing steps and segmenting the motion activity data into windows to produce segmented motion activity data;
        extract sensor specific features from the segmented motion activity data to produce extracted sensor specific features;
        generate an updated motion activity classifier function from the extracted sensor specific features;
        collect subsequent motion activity data from the at least one sensor of the at least one sensing device; and
        apply the updated motion activity classifier function to the subsequent motion activity data to produce an updated motion activity posteriorgram.

10. The sensor chip of claim 9, wherein the control circuit is further configured to store the collected motion activity data in a training data set; and wherein the updated motion activity classifier function is generated based upon the training data set.

11. The sensor chip of claim 10, wherein the training data set also includes generalized motion activity data.

12. The sensor chip of claim 11, wherein the initial motion activity classifier function is based upon the generalized motion activity data.

13. The sensor chip of claim 10, wherein the control circuit is further configured to store the collected motion activity data in a training data set; and wherein the updated motion activity classifier function is generated based upon the training data set.

14. The sensor chip of claim 9, wherein the initial motion activity classifier function is based upon generalized motion activity data.

15. The sensor chip of claim 9, wherein the control circuit is further configured to generate a data selection confidence measure after generating the initial motion activity posteriorgram; wherein the control circuit stores the collected motion activity data in a training data set if the data selection confidence measure is less than an upper threshold, and wherein the control circuit does not store the collected motion activity data in the training data set if the data selection confidence measure is greater than the upper threshold.

16. The sensor chip of claim 9, wherein the control circuit is further configured to store the collected motion activity data in a training data set, determine whether the training data set contains sufficient data prior to updating the motion activity classifier function, and not determine the motion activity classifier function unless the training data set contains sufficient data.

* * * * *